(12) United States Patent
Donohoe

(10) Patent No.: US 10,016,158 B2
(45) Date of Patent: Jul. 10, 2018

(54) ROWING FORCE AND ROWING PERFORMANCE MONITORING DEVICE

(71) Applicant: RhoForce LLC, Edgewood, PA (US)

(72) Inventor: Thomas J. Donohoe, Pittsburgh, PA (US)

(73) Assignee: RhoForce LLC, Edgewood, PA (US)

( * ) Notice: Subject to any disclaimer, the term of this patent is extended or adjusted under 35 U.S.C. 154(b) by 155 days.

(21) Appl. No.: 15/063,573

(22) Filed: Mar. 8, 2016

(65) Prior Publication Data

US 2016/0263438 A1 Sep. 15, 2016

Related U.S. Application Data

(60) Provisional application No. 62/130,029, filed on Mar. 9, 2015.

(51) Int. Cl.

| | | |
|---|---|---|
| *A63B 69/06* | (2006.01) | |
| *A61B 5/22* | (2006.01) | |
| *B63H 16/06* | (2006.01) | |
| *G09B 19/00* | (2006.01) | |
| *A61B 5/00* | (2006.01) | |
| *H02N 2/18* | (2006.01) | |

(52) U.S. Cl.
CPC ............ *A61B 5/224* (2013.01); *A61B 5/6895* (2013.01); *A63B 69/06* (2013.01); *B63H 16/06* (2013.01); *G09B 19/0038* (2013.01); *H02N 2/18* (2013.01)

(58) Field of Classification Search
CPC .............. A63B 69/06; A63B 2069/062; A63B 2069/064; A63B 2069/066; A63B 2069/068; A63B 22/0076; A63B 2022/0079; A63B 2022/0082; A63B 2022/0084; B63H 16/06; B63H 16/04; B63H 16/067; B63H 16/073; B63H 2016/043; B63H 2016/046; B63H 2016/063

See application file for complete search history.

(56) References Cited

U.S. PATENT DOCUMENTS

| | | | | |
|---|---|---|---|---|
| 7,114,398 B2* | 10/2006 | Haines | ................... | A63B 24/00 440/106 |
| 7,207,853 B2* | 4/2007 | Spencert | ................. | B63B 35/71 440/21 |
| 8,036,826 B2* | 10/2011 | MacIntosh | ......... | A63B 24/0021 701/25 |
| 8,192,242 B2* | 6/2012 | Luecker | ................. | A61B 5/224 440/101 |
| 8,968,041 B2* | 3/2015 | Rubbo | ................... | B63H 16/04 440/2 |

(Continued)

*Primary Examiner* — Justin Olamit

(74) *Attorney, Agent, or Firm* — Keevican Weiss & Bauerle LLC; Jeffrey D. Mulrooney, Esq.

(57) ABSTRACT

A force measurement device capable of wirelessly transmitting information about strokes produced by a rower rowing a boat. The device itself attaches to an oarlock without requiring any modification to the oarlock, riggers, or boat. One device shall be required per oarlock. The device may be self powered or utilize an energy storage device.
The device will transmit the information gathered by the sensors via wireless communications to a smart device in the boat or a nearby location. This smart device will display the information in a manner easily interpreted to the user, store received data and transmit the data.

10 Claims, 11 Drawing Sheets

(56) References Cited

U.S. PATENT DOCUMENTS

2005/0215870 A1\* 9/2005 Rademaker ............. A61B 5/00
                                                          600/301
2012/0276508 A1   11/2012 Jacobsen \* cited by examiner

ROWING FORCE AND ROWING PERFORMANCE MONITORING DEVICE

CROSS-REFERENCE TO RELATED APPLICATION

This application is related to and claims priority from U.S. Provisional Patent Application No. 62/130,029, entitled "Rowing Force and Rowing Performance Monitoring Device" which was filed Mar. 9, 2015 and is hereby incorporated by reference in its entirety.

BACKGROUND OF THE INVENTION

The primary goal of competitive rowing is to make a human-powered boat travel through the water as fast and efficiently as possible. An efficient boat will have rowers that are synchronous in both their movement and power application on the oar.

To increase boat speed, coaches must address the technique and timing of individual rowers. Coaches traditionally have had to rely solely on visual observations to evaluate the technical issues of rowers. Unlike indoor rowing machines, a rower, coxswain or coach cannot quantify an individual's power application or stroke timing. The lack of objective data makes the delivery of concise coaching feedback difficult. In a sport where races are often won and lost within fractions of a second, additional information about the power and timing of strokes would be very beneficial. Currently, only highly specialized electronic equipment, out of reach of most regular rowing clubs and teams, is able to provide an answer to this need.

SUMMARY OF INVENTION

The present invention is a device that attaches to an oarlock and measures the force applied by a single rower to the inner surface of the oarlock. The device is designed to operate without external wires or any modification to existing rowing equipment. Instead, the device can be attached to an existing oarlock by employing a reusable locking system.

In principle, the device can be self-powered by using the energy of the compressive force applied by the oar and piezoelectric components within the device to generate an electric potential. Units without the self-powered system will run on battery or other energy storage device.

The device can feature circuitry that will detect changes in device orientation such as an internal compass or accelerometer. The orientation sensors will work in tandem with an orientation from the smartphone or tablet to determine catch and release angles of each rower relative to the racing shell.

A network of these devices is used in each boat, one for each oarlock. Each sensor will communicate wirelessly with a single data collection hub located in the boat. The data collection hub will be a smartphone or tablet. The information received by the smartphone or tablet shall be processed by software resident on the device. This software will be able to display data from the most recent stroke.

In one embodiment, the invention is a force measurement device for use with an oarlock of a boat, the force measurement device including at least one force sensing element disposed on a housing configured to secure to an oarlock, wherein the at least one force sensing element is positioned to contact an oar shaft when the oarlock is being used for rowing, and wherein the at least one force sensing element is configured to measure the force applied thereto by the movement of the oar shaft. In another embodiment, the device further includes a piezoelectric element configured to produce an electrical potential from force applied by the oar shaft, and the electrical potential is used to power the device. In another embodiment the device further includes an accelerometer and/or digital compass which when used with other devices and a smartphone, can determine catch and release angles of each rower. In another embodiment the device further includes at least one microprocessor in communication therewith configured to run software that can display force information in the form of gradients. In another embodiment the device further includes at least one microprocessor in communication therewith configured to run software that can indicate information about the timing of an individual rower's stroke relative to a stroke seat. In another embodiment the device further includes a gravity toggle switch configured to deactivate the device when the device is inverted relative to an activated position. In another embodiment the device further includes at least one microprocessor in communication therewith configured to run software that offers a different possibility of actions based on the user type, the user types are chosen from group comprising a coxswain, a rower, and a coach.

BRIEF DESCRIPTION OF THE INVENTION

Figure 1:
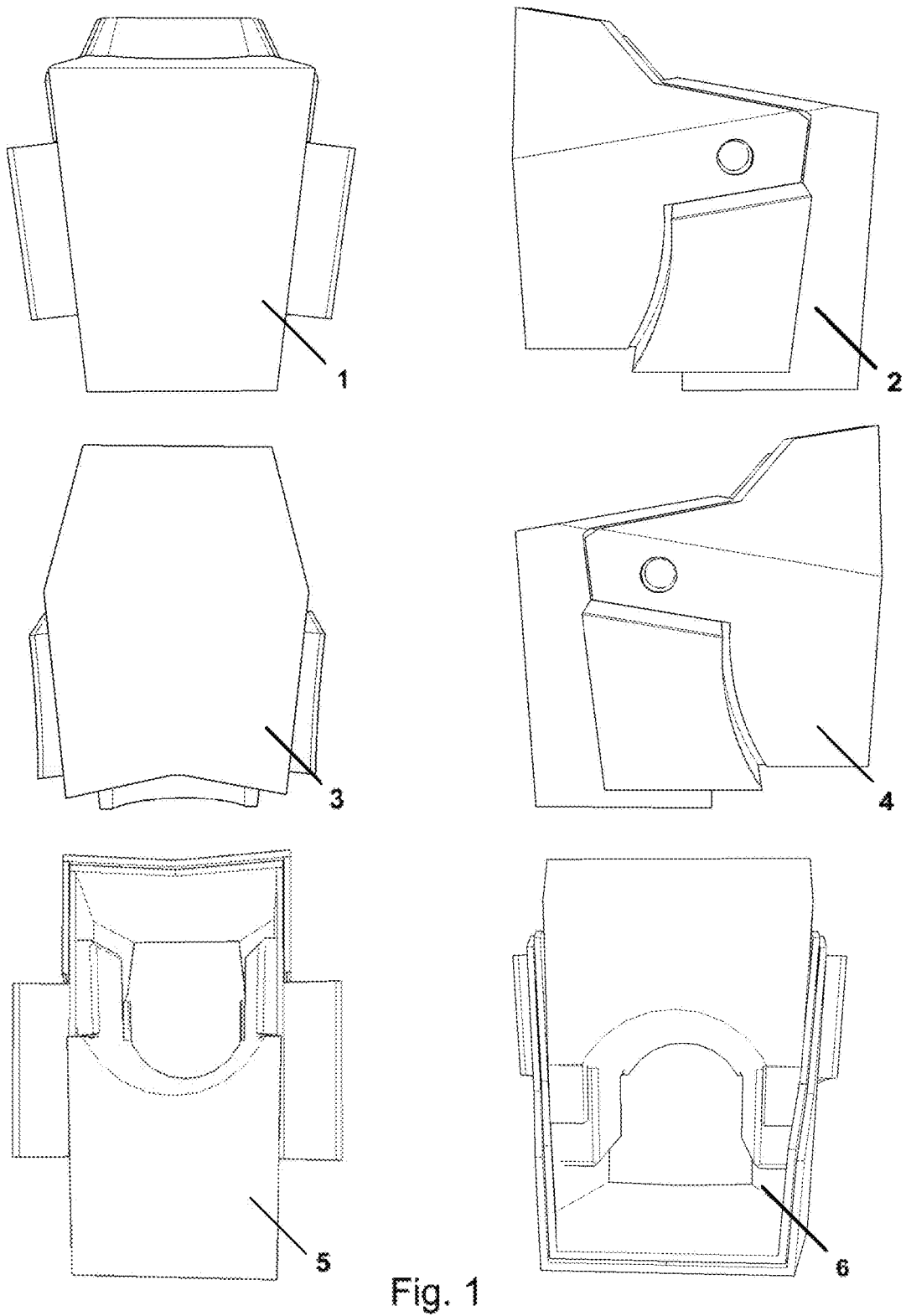
FIG. 1 Shows rear, front, right side, left side, top and bottom views of the device according to an embodiment of the present invention.

The present invention provides for a device that attaches to an oarlock and measures the force applied by a single rower to the inner surface of the oarlock. The device is designed to operate without any external wires or any modification to existing rowing equipment. The device can be secured to an oarlock by employing a reusable locking system.

These and other features and characteristics of the present invention, as well as the methods of operation and functions of the related elements of structures and the combination of parts and economies of manufacture, will become more apparent upon consideration of the following description with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification, the singular form of "a", "an", and "the" include plural referents unless the context clearly dictates otherwise.

Referring generally to FIGS. 1-5 and more particularly to FIG. 1, the general appearance of an assembled device housing according to an embodiment of the invention from all six directions, rear 1, right side 2, front 3, left side 4, bottom 5 and top 6 is shown. FIG. 1 does not include an oarlock 7 that the device would typically attach to during use.

Figure 2:
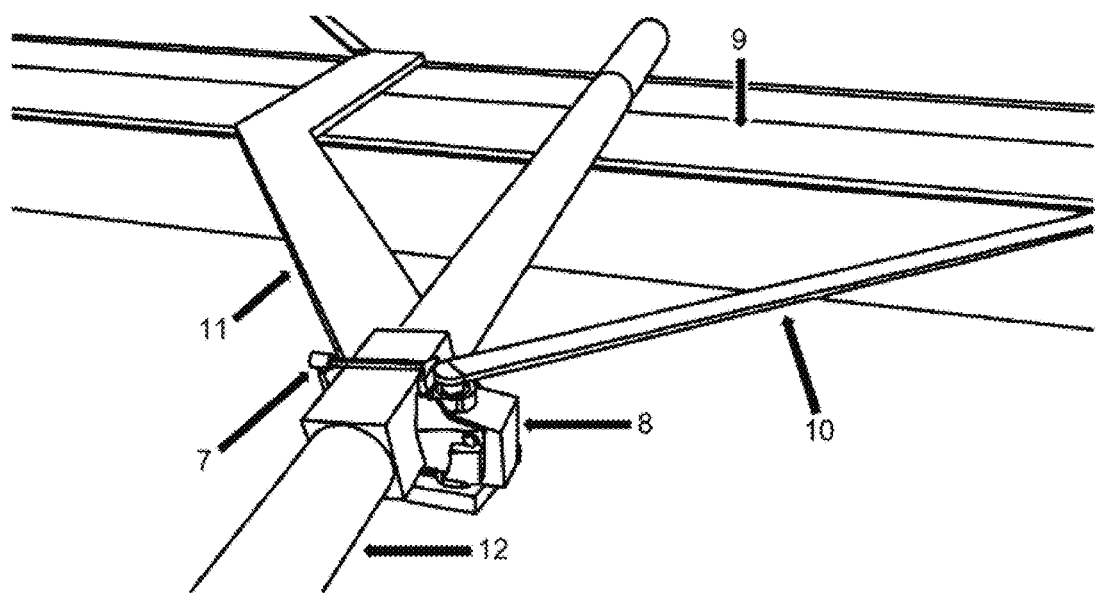
FIG. 2 Shows a perspective view of the invented device mounted on a racing shell.

Referring to FIG. 2, an assembled device 8 is portrayed mounted on a racing shell. The device 8 attaches to the oarlock 7. The oarlock 7 is connected to the rest of the racing shell 9 via the backstay 10 and rigger 11. Oar shaft 12 is shown being held by the oarlock 7.

Figure 3:
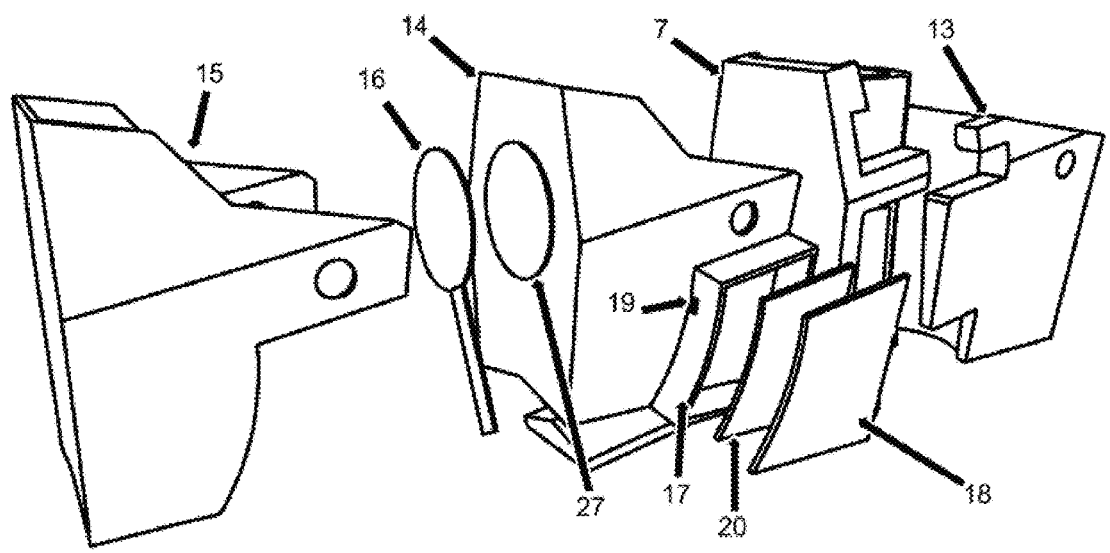
FIG. 3 Shows an exploded view of the present invention.
Figure 4:
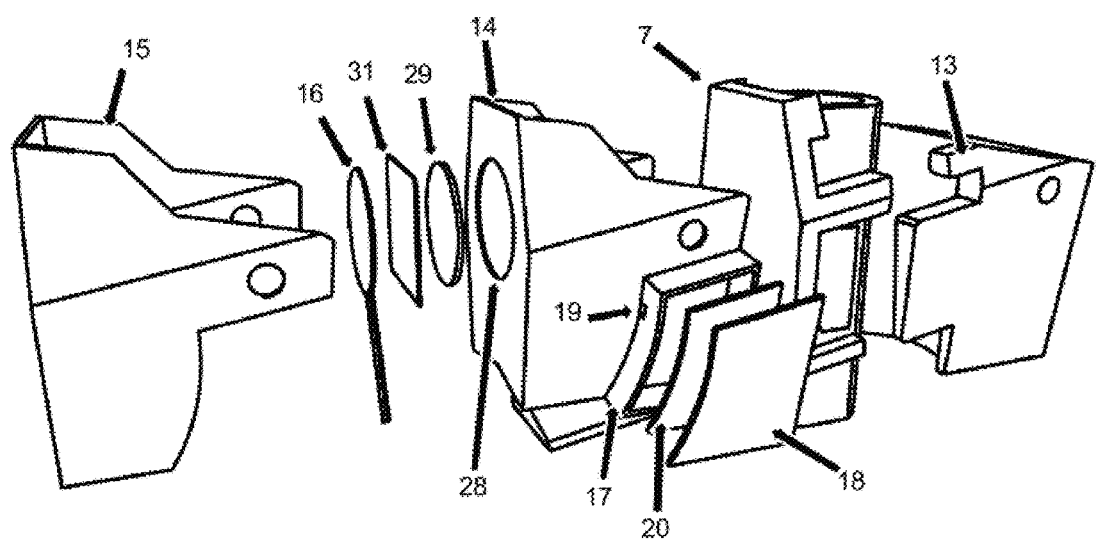
FIG. 4 Shows an exploded view of the device with power generating piezoelectric components included according to an embodiment of the present invention.

Referring to FIG. 3 and FIG. 4, which depict two versions of the device. FIG. 3 depicts a battery powered version while FIG. 4 depicts a self powered version. Oarlock 7 in both figures is a partial mockup of a commonly used Concept II oarlock surrounded by the device components and is included for reference. Since both versions will attach to the same style of oarlock, they can be made up of the same three casing elements, the rear anchor 13, the inner sleeve 14, and the outer sleeve 15.

The rear anchor 13 may be made of a hard plastic. Its role is to firmly slide onto the oarlock 7 and provide a base for the rest of the device to attach via a pin or bolt. The rear anchor 13 also serves to protect the rest of the device from impact. Any force that is provided to the rear of the device or the side will dissipate through the rear anchor 13.

Inner sleeve 14 shall be constructed with durable plastic and outer sleeve 15 shall be constructed of durable, weather resistant metal. These two components will be adhered to one another using a flexible bonding agent. Together the inner 14 and outer sleeve 15 protect the sensing element 16 encased within. The combined thickness of the inner sleeve 14 and outer sleeve 15 sleeve should be no greater than 4 mm as to not impede proper rotation of the oar shaft 12 within the oarlock 7. Attached to the inner sleeve 14 are two electrical component boxes 17 with lids 18 that form a watertight seal. Both electrical component boxes 17 feature a small hole 19 from which power supply and sensor wires will run. With one electrical component box 17 on each side of the device, one houses a power supply and the other a circuit board 20. The power supply and circuit board 20 are placed opposite each other in different sides of the device in the electrical component boxes 17.

Figure 5:
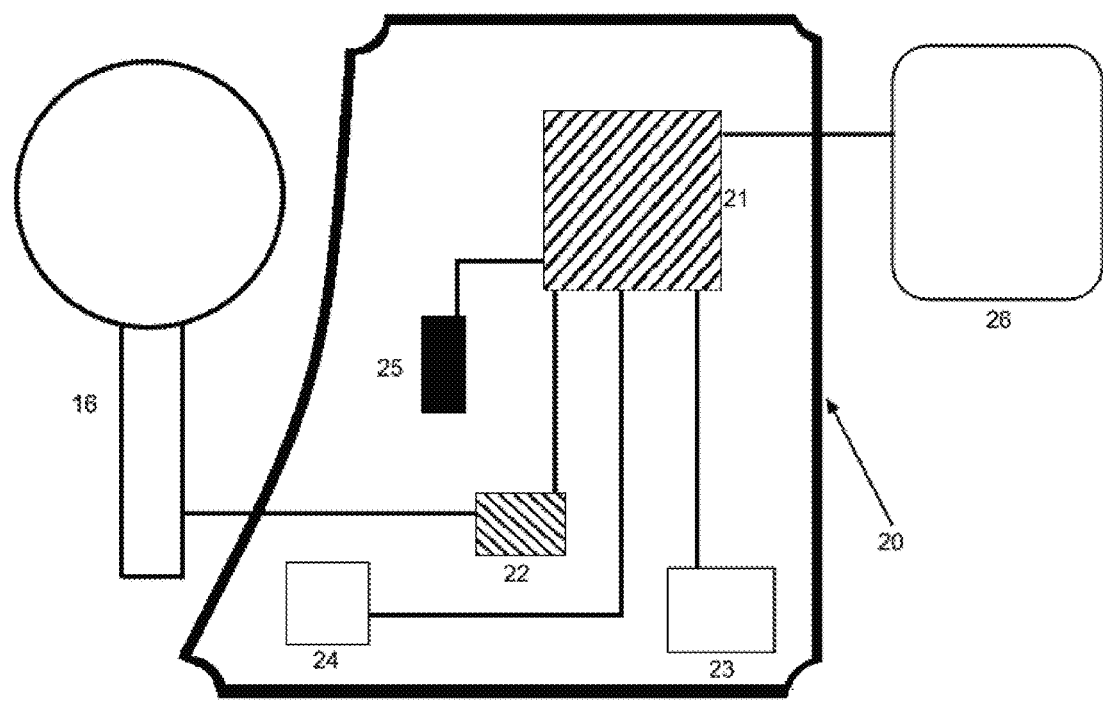
FIG. 5 Shows a two dimensional view of a potential electronics arrangements on an embedded, multi-layer printed circuit board along with external connections.

Referring to FIG. 5, a two dimensional representation of a potential circuit board arrangement is seen. Items on the circuit board 20 include, but are not limited to, a wireless transmission device 21, an amplifier circuit for the sensor 22, a digital compass 23 and/or an accelerometer 24 and gravity toggle switch 25. Each device is connected to the central transmission device 21. The amplifier circuit for the sensor 22 makes a connection to the force sensor 16 off of the circuit board. A power supply 26 is also attached to the central transmission device, but it is not integral to the circuit board 20. The power supply 26 could either be a battery or power converter depending on the embodiment of the invention.

The inner sleeve 14 in FIG. 3 and FIG. 4 differ in a small way. In FIG. 3, the cylindrical outcrop 27 has the same footprint as the force sensor 16 and is designed to focus the applied load on the sensor 16. In FIG. 4, the cylindrical indentation 28 houses the base of the piezoelectric component 29 which is the same footprint as the force sensor 16. In the FIG. 4 setup, the piezoelectric component 29 serves as a power generation component and a method of concentrating all force from the oar 12 onto the sensor 16.

FIG. 4 has a similar circuitry configuration to FIG. 3, the majority of the hardware will be located in the circuit boxes 17. Key differences are that the electrical component boxes 17 houses a power converter 30 that translates the energy received from the piezoelectric components 29 to a usable form. The power converter 30 is housed in the opposite electrical component box 17 that houses the circuit board 20. Between the inner 14 sleeve and outer 15 sleeve, sensing elements 16 and piezoelectric transducers 29 is a thin rubber sheet 31 to insulate the components from each other and ensure proper force distribution.

The power converter is used to convert the high voltage, low current output of the piezoelectric element, and may consist of an arrangement of capacitors and a voltage regulator. The capacitors may be configured to allow charging in series and discharging in parallel. Such an arrangement would increase the supplied current and decrease the supplied voltage. A voltage regulator can then be used to equalize the energy input into the energy storage device.

Another component included in the system is a gravity toggle switch 25. Typically, when racing shells are not in use they are stored inverted. As a result of this inversion, all oarlocks are also completely inverted. An optional gravity toggle switch will be employed to ensure that the devices are deactivated when not in use. Since many boats are often stored at an inconvenient height, if a rower or coach neglects to deactivate a sensor, it will have already been turned off when the boat was taken out of the water and inverted for ease of transportation.

Also included in an embodiment of the device is a digital compass 23 and/or accelerometer 24. These two components will observe the rotation of the device, and subsequently the oarlock, over the course of the stroke. These data, when used in tandem with a bearing provided by the smartphone, will provide catch and release angles of each rower relative to the boat.

All variations of the device shall communicate with a smartphone or tablet located in or near the boat. Transmission shall be conducted via low energy wireless technology. Several embodiments employ a low energy Bluetooth system. To ensure that energy is saved while information is transmitted from the devices to the receiver, the devices will be cycled through transmission modes. This cycling will also allow all devices to have an opportunity to communicate with the master device. Further sleep modes can be applied to the devices if they are not in use for a period of time, or if they are prompted to sleep by the application on the smartphone.

Data received by the smartphone or tablet can then be processed and displayed by our application. An individual who uses the app described herein will have three profile types to choose from: rower 32, coxswain 33 or coach 34. Each profile type has a corresponding display and options for connecting to devices.

Figure 6:
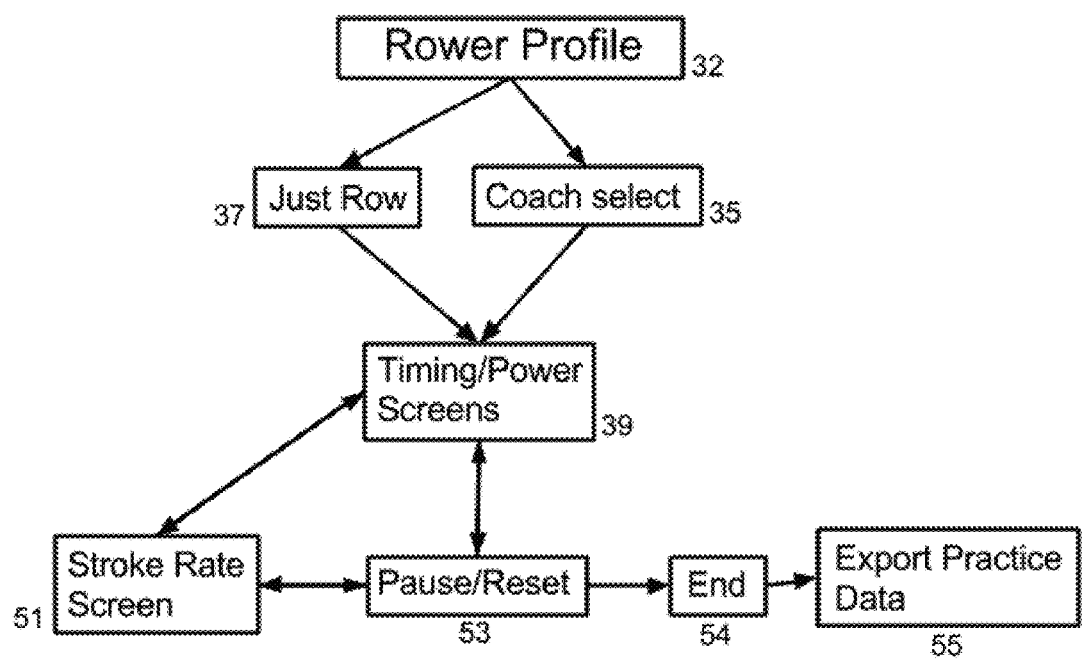
FIG. 6 Shows a software flow diagram for the Rower user setting according to an embodiment of the present invention.
Figure 7:
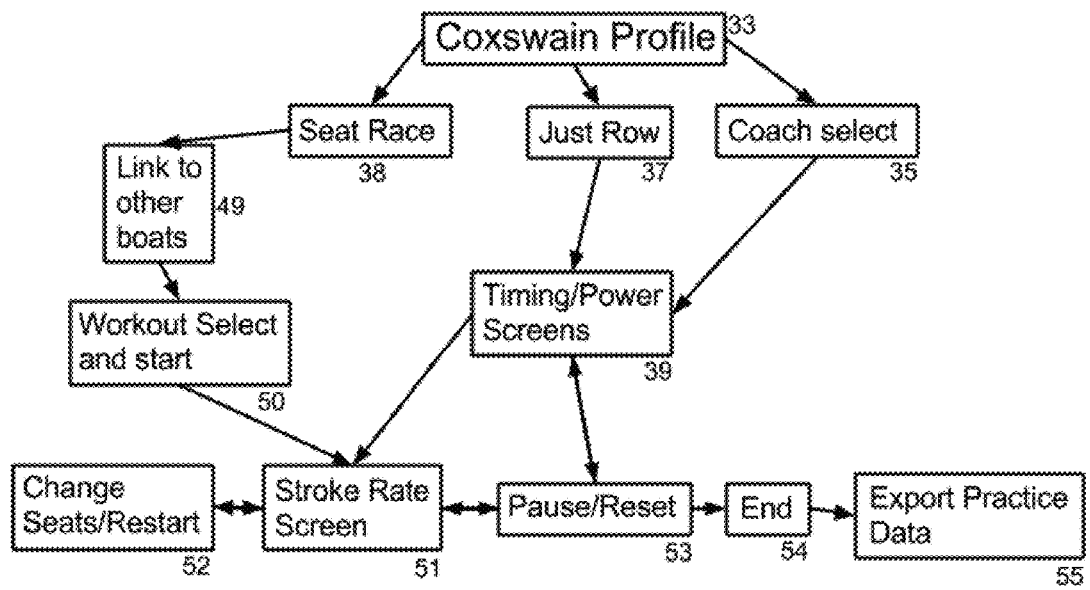
FIG. 7 Shows a software flow diagram for the Coxswain user setting according to an embodiment of the present invention.
Figure 8:
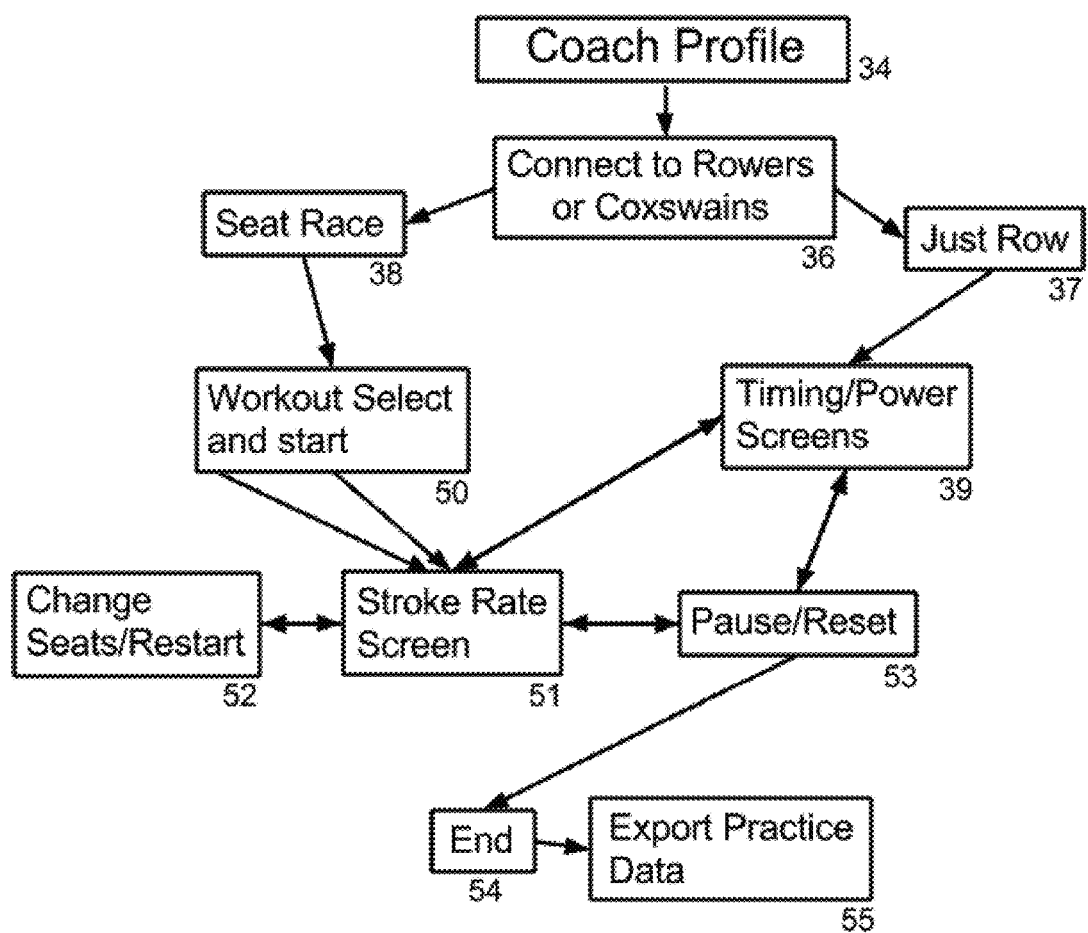
FIG. 8 Shows a software flow diagram for the Coach user setting according to an embodiment of the present invention.

Now referring to FIG. 6, FIG. 7 and FIG. 8, which show flow diagrams for each profile described herein. Rowers 32 and coxswains 33 will be able to connect via coach select 35 to devices and several coaches 34. Coaches 34 will be able to connect to coxswains 33 and rowers 32 and 36. Coaches 34 will not be given the option to connect to any devices due to a coach's dynamic proximity to their boats and devices.

After the user has selected a profile and connected their smartphone or tablet to the force measuring devices on the oarlocks, the user will be prompted to choose one of two operation formats, "just row" 37 or "seat race" 38. Rowers 32 will not be given this prompt, they will be sent directly to the "just row" 37 function.

Figure 9:
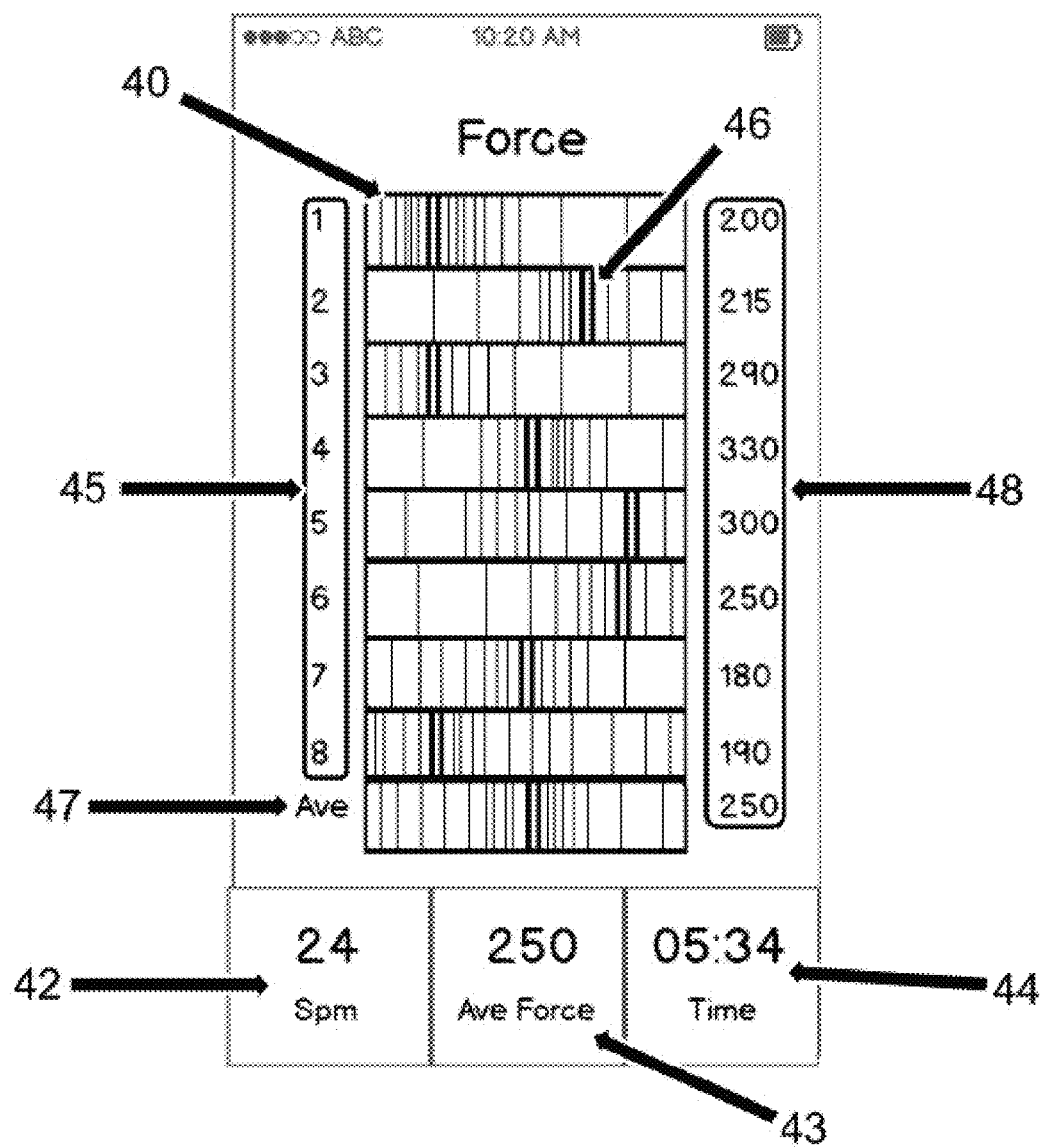
FIG. 9 Shows an application screen showing power gradients according to an embodiment of the present invention.
Figure 10:
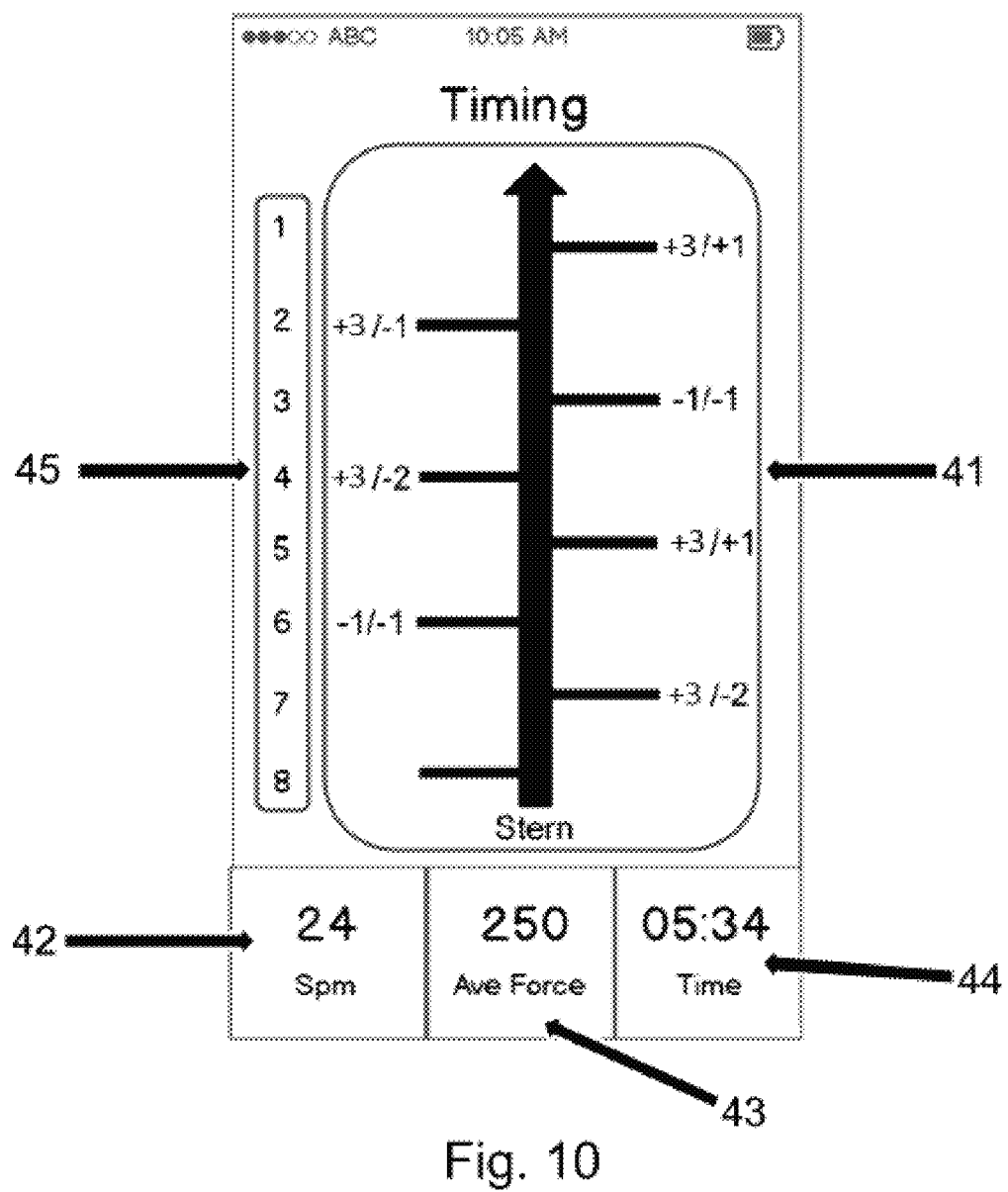
FIG. 10 Shows an application screen displaying rower timing according to an embodiment of the present invention.

The display for "just row" 37 will consist of two screens, FIG. 9 and FIG. 10. These screens are the "Timing/Power Screens" 39 and they each have different graphical information displays 40 & 41 but identical values in the bottom boxes 42, 43 & 44. The values in the bottom boxes 42, 43 & 44 have been selected as the most useful indicators of performance. The number of strokes per minute 42, the average force applied by the rowers to the oarlocks 43 and the amount of time passed 44 are the values that will be consistently present during application use. The timer 44 can be programmed to count down, count up, pause, repeat pieces or create custom workouts.

The graphical information displays 40 & 41 transition between each other automatically after a set period of time or at the command of a user's swipe. Both screens in FIG. 9 and FIG. 10 are designed to show the performance of individuals relative to the other athletes. The seat number bar 45 indicates which data corresponds to a device/rower. Numbers can be replaced with names or initials in a customization screen. The orientation of the numbers will depend on the user profile. Coxswains and coaches can view the numbers in descending order while rowers will see the numbers in ascending order. This is done to match the perspective of the user.

FIG. 9 is the Power screen. It differs from FIG. 10 in the center graphic display 40 & 41. The center graphic display in the Power Screen FIG. 9 is called the Force Gradient 40. The Force Gradient displays the output of sensors of a single boat over the course of a single stroke. A color range will be pre established based off of the type of rower in the boat. A heavyweight, experienced group of rowers will have a broader, higher range than a lightweight, inexperienced crew. For example, the experienced, heavyweight crew could have the color spectrum be based on a range of 100 lb to 400 lb. The inexperienced, lightweight crew, however, might have their force range start at 50 lb and max out at 300 lb. Both crews would see the same spectrum of colors, but the colors would represent different ranges and values. The application will compile gradients for all of the rowers in the boat based off of the pre established rower type and how hard they are pulling.

The gradients will also have a marker 46 overlaid on top of the portion of the stroke that represent the peak force exerted by each rower. The gradients on a sculler's screen will be displayed in the same fashion, however there will be two gradients per rower, one for each oar.

Below all other gradients in the Power Screen FIG. 9 is the Average Force Gradient 47. The Average Force Gradient 47 is the average of all sensor inputs from the boat over the course of a single stroke. The Average Force Gradient 47 is colored relative to the rest of the gradients. The numbers on the right side of the screen 48 represent the impulse of a single rower. The impulse values 48 are intended to be a quantitative aid for coaches and rowers. The impulse values 48 will indicate which rowers are pulling the hardest and which rowers are pulling the least.

The Timing Screen, FIG. 10, has similar features to the Power Screen FIG. 9. It has a seat number bar 45 on one side and the same key measurements 42, 43 & 44 on the bottom of the screen. The key purpose of the graphical information display 41 on the Timing Screen is to indicate when rowers are catching and releasing relative to the stroke seat. Excluding the stroke seat, each rower has two numbers associated with their seat. The first number represents the catch timing and the second represents the release timing. Both numbers are relative and do not necessarily represent seconds. Pluses and minus will be used to indicate when a rower is early or late compared to stroke seat. If a rower is early or late beyond a given tolerance, the text of the outlier will be displayed in a different color and bigger font. Just as it does in FIG. 9, the orientation of the seat numbers 45 and the information display 41 conform to the user type chosen.

Figure 11:
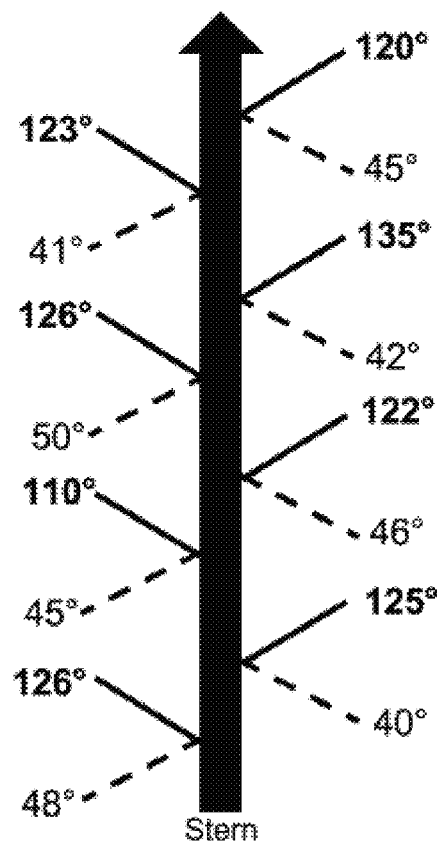
FIG. 11 Shows an application screen displaying rower catch and release angles according to an embodiment of the present invention.

Another screen, the Catch and Release Angle Screen, can be viewed by the user anytime they are viewing either the Power Screen or Timing Screen. FIG. 11 is the potential appearance of such a screen. Similar to the timing screen, an arrow represents the direction of boat travel and each seat is shown in the appropriate order. Each seat has a solid line and a dashed line related to it along with two numbers. The dashed line and the adjacent number represent release angle while the solid line and adjacent number represent catch angle.

The other mode of operation, Seat Racing 38, will only be enabled in coxswain 33 or coach 34 mode. A seat race is a widely practiced method for determining the speed of individual rowers relative to each other. Multiple races of fixed duration or distance are performed and rower lineups are typically changed with each race. By comparing margins of victory between pieces and which rowers have been switched, a coach can establish rower skill relative to other rowers in the crews.

To clarify the process of seat racing and the deductions the software will make, an example of a seat race between two hypothetical rowers will be used. Rower Alpha and rower Beta are in two different eight man shells which are competing in a series of five minutes races against each other. Both rowers are sitting in the bow seat of their respective boats. The rest of the seats in the boats are filled with athletes who will remain in the same seat for all of the races. The first race begins. During the race the smartphones located in the boats record data about the boat's peak velocity, average velocity, total distance traveled and how hard each rower is pulling. At the end of the first race, the phone prompts the administrator of the seat race to indicate which rowers they would like to switch along with any additional notes they may have. Rower Alpha and Beta switch positions with each other and the administrator of the seat race notes the rower swap in their smartphone.

Another race is performed, The smartphones record the same data as before and the coach is prompted to enter any notes they might have. These notes could be water conditions, differences in rower technique or the margin of victory visually observed. By comparing the relative spacing of the boats in both races, the application will deduce how each rower changed the performance of each boat. Typically the only comparison done in a seat race is the apparent margin visually observed by the coach. Unfortunately, this visual analysis can be inaccurate due to one coxswain steering a longer course than the other, or by the coach inconsistently observing margins between boats. By using velocity and distance data provided by the smartphone gps, the application will reduce human error and provide more accurate feedback.

The application will also keep a track of the relative rank of rowers that have been switched. For example, if a third rower was introduced, rower Gamma, and over the course of several seat races rower Gamma is determined to be faster than rower Alpha, and rower Alpha is already known to be faster than rower Beta, the application would then infer that rower Gamma would likely be faster than rower Beta if they were directly seat raced. The degree to which one rower is "faster" than another will also be quantified by the app by comparing velocity data from both boats. Such information could be displayed as a speed.

When a coach 34 or coxswain 33 selects the option to perform a seat race, they will be given the option to select boats to link 49 with. When a coxswain 33 selects to Seat Race, the coxswain 33 that initiates the linking process will become the administrator of the seat race. All other boats that connect to the administrator will rely on it for workout instruction. When a coach 34 links to a rower 32 or coxswain 33 or set of crews, the coach will automatically become the administrator of the Seat Race.

After the smart devices have been connected, the administrator will be able to select from a list of pre-established and custom Seat Race workouts. Once the administrator has prepared the crew for the piece, the administrator will start the piece using his device 50. All smart devices connected to the administrator will display a synchronized countdown to begin the piece. During the piece, the coxswains will be given a simplified display which only features the stroke rate 51 of their boat and the time remaining in the piece. Administrators will be given a similar screen 51, but with the stroke rates of all the boats they are connected to along with the ability to pause or restart the pieces. Non-administrators will not be able to pause or restart the piece.

Once a piece has ended, the administrator will be shown a summary of the piece, any rowers that pull inconsistently will be indicated. The administrator will also be prompted to select which seats they switch 52 and make any notes they desire. The process will continue until the administrator exits Seat Race mode or the pre-programmed workout ends. The application will keep track of all force data, seat changes, manually entered observations from the coach and relative boat speeds recorded by the in boat smartphones. The administrator's smartphone will use the recorded data to deduce the speed of rowers relative to each other.

Once a team has completed a practice, the user can select "Pause/Reset" menu 53. From there, the user will be given the option "End" 54 the session and export the data from their practice 55. Data can be exported to another device or to an email address provided by the user. Coxswains and rowers can export data on their boat, coaches can export recorded data from all devices to which they are connected. The exported data shall include, but not be limited to: breakouts of pieces, average stroke rates, average boat speed, distance traveled, average power output by boat and rowers, average timing of rowers and any comments supplied by a coach. A report from a seat race practice will contain more detailed feedback on the performance of individual rowers. Rowers that are inconsistent with their power application and timing during pieces will be indicated.

Although the invention has been described in detail for the purpose of illustration based on what is currently considered to be the most practical and preferred embodiment of the app, it is to be understood that such detail is solely for that purpose and that the invention is not limited to the described embodiment. To the contrary, it is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A force measurement system for use with an oarlock of a boat defining an opening configured to receive an oar shaft, the force measurement system comprising:
    at least one force sensor disposed on a housing configured to secure to an oarlock by surrounding a portion of the oarlock, wherein the at least one force sensor is in mechanical communication with an oar shaft when the oarlock is being used for rowing,
    wherein the at least one force sensor is configured to measure a force applied to the force sensor by the oar shaft
    wherein the force sensor is disposed on the oarlock within an opening defined by the oarlock, and
    wherein the opening is configured to receive the oar shaft.

2. The force measurement system of claim 1, further comprising a piezoelectric element configured to produce an electrical potential from force applied by the oar shaft, and wherein the electrical potential is used to power the device.

3. The force measurement system of claim 1, further comprising at least one microprocessor in communication with the force sensor, the at least one processor configured to run software that can display force information in a form of gradients.

4. The force measurement system of claim 1, further comprising at least one microprocessor in communication with the force sensor, the at least one processor configured to run software that can indicate information about a timing of an individual rower's stroke relative to a stroke seat.

5. The force measurement system of claim 1, further comprising a gravity toggle switch configured to deactivate the device when the device is inverted relative to an activated position.

6. The force measurement system of claim 1, further comprising at least one microprocessor in communication with the force sensor, the at least one processor configured to run software that offers a different possibility of actions based on a user type, wherein the user type is chosen from a group consisting of a coxswain, a rower, and a coach.

7. The force measurement system of claim 1, further comprising at least one accelerometer.

8. The force measurement system of claim 1, further comprising at least one electronic compass.

9. The force measurement system of claim 1, further comprising at least one accelerometer and at least one electronic compass.

10. The force measurement system of claim 1, wherein the housing secures to the oarloack by engagement with an anchor element, and
    wherein the housing and anchor element jointly encircle a pin of the oarlock.

* * * * *